(12) United States Patent
Zhu et al.

(10) Patent No.: US 9,596,847 B2
(45) Date of Patent: *Mar. 21, 2017

(54) ALKOXYLATED ALKYLAMINE QUATERNARY SURFACTANTS FOR GLYPHOSATE

(71) Applicant: Monsanto Technology LLC, St. Louis, MO (US)

(72) Inventors: Shawn Zhu, Stormville, NY (US); William Abraham, Wildwood, MO (US); John Hemminghaus, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 54 days.

This patent is subject to a terminal disclaimer.

(21) Appl. No.: 14/242,280

(22) Filed: Apr. 1, 2014

(65) Prior Publication Data

US 2014/0213451 A1    Jul. 31, 2014

Related U.S. Application Data

(62) Division of application No. 11/575,800, filed as application No. PCT/US2005/034076 on Sep. 23, 2005, now Pat. No. 8,722,581.

(60) Provisional application No. 60/612,598, filed on Sep. 23, 2004.

(51) Int. Cl.
    *A01N 57/18* (2006.01)
    *A01N 25/30* (2006.01)
    *A01N 57/20* (2006.01)

(52) U.S. Cl.
    CPC ............. *A01N 25/30* (2013.01); *A01N 57/20* (2013.01)

(58) Field of Classification Search
    None
    See application file for complete search history.

(56) References Cited

U.S. PATENT DOCUMENTS

| 5,317,003 A | 5/1994 | Kassebaum et al. |
| 5,462,912 A | 10/1995 | Hioki et al. |
| 5,998,332 A | 12/1999 | Sato et al. |
| 6,770,608 B2 | 8/2004 | Franklin et al. |
| 7,723,265 B2 * | 5/2010 | Xu .......... A01N 37/04 504/127 |
| 8,722,581 B2 * | 5/2014 | Zhu .......... A01N 25/30 504/206 |
| 2003/0104943 A1 | 6/2003 | Lennon et al. |
| 2006/0040826 A1 | 2/2006 | Eaton et al. |

FOREIGN PATENT DOCUMENTS

| EP | 0274369 A1 | 7/1988 |
| EP | 0526444 A1 | 2/1993 |
| EP | 0582561 A1 | 2/1994 |
| WO | 9402021 | 2/1994 |
| WO | 9732476 | 9/1997 |
| WO | 9904635 | 2/1999 |
| WO | 2005016002 | 2/2005 |

OTHER PUBLICATIONS

Akzo Chemie America, "Physical and Chemical Characteristics of Armak Ethoxylated Aliphatic Chemicals", Bulletin 85-10, 1985, 15 pages.
Laerke, P.E. et al., "Foliar Absorption of Some Glyphosate Formulations and their Efficacy on Plants", Pestic. Sci., (1995), pp. 107-116, vol. 44.
Wyrill, J.B. III et al., "Glyphosate Toxicity to Common Milkweed and Hemp Dogbane as Influenced by Surfactants", Weed Science, (1977), pp. 275-287, vol. 25:3.
International Search Report and Written Opinion issued in connection with PCT/US2005/034076, dated Feb. 6, 2006.
Extended European Search Report, EP Application No. 15190163.4-1454, dated Apr. 16, 2016, 9 pages.

* cited by examiner

*Primary Examiner* — Alton Pryor
(74) *Attorney, Agent, or Firm* — Senniger Powers LLP; Erin C. Robert (57) ABSTRACT

The present invention relates to stable glyphosate formulations with improved efficacy by a highly effective alkoxylated alkylamine quaternary surfactant at a very low used level. The alkoxylated alkylamine quaternary surfactant is compatible in all salts of glyphosate formulations (including potassium and ammonium) even at very high concentration (470-600 g a.e./l).

31 Claims, 3 Drawing Sheets

ALKOXYLATED ALKYLAMINE QUATERNARY SURFACTANTS FOR GLYPHOSATE

REFERENCE TO RELATED APPLICATIONS

This application is a divisional of U.S. patent application Ser. No. 11/575,800, filed Oct. 2, 2008, which is the U.S. National Stage Application of PCT/US2005/034076, filed Sep. 23, 2005, which claims the benefit of U.S. Provisional Application Ser. No. 60/612,598, filed Sep. 23, 2004, the entire contents of which are hereby incorporated by reference for all relevant purposes.

FIELD OF THE INVENTION

The present invention relates to glyphosate formulations comprising alkoxylated alkylamine quaternary surfactants having improved herbicidal activity.

BACKGROUND OF THE INVENTION

N-phosphonomethylglycine, otherwise known as glyphosate, is well known in the art as an effective post-emergent foliar applied herbicide. Glyphosate is an organic compound with three acidic groups, and in its acid form is relatively insoluble in water. Glyphosate is, therefore, normally formulated and applied as a water-soluble salt. Although monobasic, dibasic and tribasic salts of glyphosate can be made, it has generally been preferred to formulate and apply glyphosate, in the form of a monobasic salt, for example as a mono-isopropylamine, mono-potassium or mono-ammonium salt, or a dibasic salt such as the diammonium salt. Glyphosate herbicidal formulations are known which effectively comprise a mixture of mono-ammonium and di-ammonium salt, i.e., where the molar ratio of ammonium ion to glyphosate anion in the formulation is between 1 and 2.

When the terms "ammonium", "monoammonium" and "diammonium" are used herein to refer to salts of glyphosate, these terms apply strictly to inorganic ammonium, i.e., $NH_4^+$, unless the context demands otherwise. Glyphosate rates and concentrations given herein, even where the glyphosate is present as a salt or salts, are expressed as acid equivalent (a.e.) unless the context demands otherwise.

For many applications, glyphosate salts require the presence of a suitable surfactant for best herbicidal performance. The surfactant can be provided either in the form of a concentrate, or it can be added by the end-user to the diluted spray solution. The choice of surfactant can be important since there are wide variations among surfactants in their ability to enhance the herbicidal efficacy of glyphosate for particular applications.

Use of a highly concentrated aqueous formulation of glyphosate in the form of a salt made with the inorganic base ammonia and potassium is advantageous. Ammonia and potassium are readily available, low in molecular weights, and relatively soluble in water. Additionally, they are natural nutrients for the growth of plants and other organisms. The use of ammonium and potassium salts of glyphosate for preparing aqueous concentrate formulations of glyphosate suitable for killing and controlling weeds and other plants has, however, been somewhat limited due to difficulties arising from chemical and physical properties of the ammonium and potassium salts of glyphosate, lack of suitable surfactants for preparing high-loaded liquid concentrates of such salts, reduced weed control, and requirement for complex processes for preparing liquid ammonium and potassium glyphosate compositions.

Accordingly, it is desirable to develop an aqueous glyphosate formulation (i) having high glyphosate a.e. loading, (ii) containing a suitable herbicidal efficacy enhancing surfactant that can be used for all salts of glyphosate, and (iii) having a optimized concentration at very low loading level of that surfactant to provide herbicidal effectiveness greater than that of commercial standard glyphosate salt formulations.

It is, therefore, an objective of the present invention to provide a storage-stable, highly concentrated aqueous formulation containing glyphosate together one or more agriculturally acceptable surfactants that enhance the herbicidal effectiveness of applications of the formulation.

It is a further objective of the present invention to provide a storage-stable, highly concentrated aqueous formulation containing glyphosate and one or more surfactants and having a superior level of herbicidal effectiveness by comparison with current commercial standard glyphosate salt formulations.

There is a particular need in the art for stable aqueous liquid formulations comprising a quaternary ammonium salt surfactant such as, e.g., a dialkoxylated dialkylammonium halide, and in particular for formulations comprising ammonium glyphosate and a dialkoxylated dialkylammonium salt surfactant. Such formulations are known to the art, but have generally required a significant fraction of a nonionic surfactant to maintain stability of the formulation. Additionally, the quaternary ammonium salt in many such formulations comprise the di(hydroxyethyl)methyl cocoamine, which is a highly effective

SUMMARY OF THE INVENTION

The present invention relates to glyphosate formulations having improved stability and bioefficacy comprising as an adjuvant, at least one alkoxylated alkylamine quaternary surfactant. The aforementioned adjuvant can be employed at low dosage rates and is stable in all of the various salts of glyphosate even at very high concentration.

DETAILED DESCRIPTION OF THE INVENTION

Glyphosate formulations generally require one or more adjuvants in order to boost its bio-efficacy. The amount of adjuvant employed is typically a glyphosate acid:adjuvant ratio of about 3:1 to 5:1 or lower in order to achieve significant boosting effect. The cost associated with the use of the adjuvants and other additives in glyphosate formulations can be significant. Therefore, there is an ever increasing need to find a more effective and economical adjuvant for glyphosate.

Glyphosate is an acid with a very limited solubility in water while salts of glyphosate have very high solubility in water. Therefore, glyphosate formulations usually employ salts of glyphosate. Many counterions have been used commercially in glyphosate products. They include isopropylamine, monoethanolamine, sodium, trimethylsulfonium, potassium, and ammonium. Accordingly, there are numerous salts of glyphosate, and many more surfactant choices used in the formulations. However, the use of too many surfactants in a glyphosate formulation plant can create logistical problems in part due to the fact that separate storage vessels are required for each surfactant. This can be costly, and thus there is a need to minimize the number of surfactants used in a glyphosate formulation plant.

For liquid concentrate glyphosate formulations, practical glyphosate loading can be 360 g a.e./l or higher. It is known to skilled in the art that not many biologically useful surfactants can be incorporated in glyphosate formulations without phase separation at the practical loading of glyphosate and surfactants, in particular in the case of potassium and ammonium salts. One of the objectives is, therefore, to find a highly efficacious surfactant that can be used at very low levels in glyphosate formulations to improve the bio-efficacy of glyphosate where the surfactant can be formulated into stable liquid concentrate formulations containing glyphosate as the potassium or ammonium salts at 470-600 g a.e./l.

The present invention meets this objective in providing glyphosate formulations having improved stability and bio-efficacy comprising, as an adjuvant, at least one alkoxylated alkylamine quaternary surfactant. The aforementioned adjuvant can be employed at low dosage rates and is stable in all of the various salts of glyphosate even at very high glyphosate concentration. In this regard it has been unexpectedly discovered that a class of surfactants exemplified by cocoamine quaternary surfactants with 2EO at a use level 3% (active quat) enhanced significantly the efficacy of glyphosate formulations in controlling unwanted weeds. It was found to be more effective than known commercial products and can be incorporated at very high loading of up to 600 g a.e./l potassium glyphosate and 470 g a.e./l ammonium glyphosate. At such high concentrations as 600 g a.e./l potassium glyphosate and 470 g a.e./l ammonium glyphosate, several of the surfactants used in current commercial glyphosate products will cause formulations to phase separate. Moreover, cocoamine-2EO quaternary surfactants are compatible with all of the various salts of glyphosate, even at very high loading.

The class of alkoxylated alkylamine quaternary surfactant adjuvants according to the present invention is represented by General Formula I, below:

wherein R is a straight or branched chain, saturated or unsaturated alkylene group having from 8 to 22 carbon atoms; R' is a straight or branched chain, saturated or unsaturated alkylene group having from 1 to 4 carbon atoms; and n+n' is an integer of from 0-30, m+m' is an integer of from 0 to 30, and z+z' is an integer of from 0-30, with the proviso that n+z is at least 1 and/or n'+z' is at least 0 or 1, and X– is a compatible anion such as methyl sulfate or Cl⁻. In a preferred embodiment, the degree of ethoxylation is at least 1 and up to 30.

A preferred cationic surfactant is methyl bis(2-hydroxyethyl)coco ammonium chloride. In certain preferred compositions of the invention the cationic surfactant is methyl bis(2-hydroxyethyl)cocoammonium chloride and there is no significant amount of secondary nonionic surfactant employed in the formulation. Nonionic surfactants such as polyoxyethylene alkylether including polyoxyethylene secondary alcohol having an average of about 3 to about 15 moles ethylene oxide at a concentration greater than 5% with a cationics to nonionic ratio less than 5.2, are specifically excluded from the formulations of the present invention.

In another embodiment, the formulation of the invention contains less than about 0.5% by weight of other surfactants; in another embodiment less than about 0.2% by weight of other surfactants; in another embodiment less than about 0.1% other surfactants, and in still another embodiment no substantial amounts of other surfactants.

The water-soluble concentrate formulations of the present invention typically contain an amount of surfactant from about 0.5% to about 10% by weight in total of one or more surfactants. Preferably about 2% to about 8% by weight of surfactant is used although greater or lesser amounts may be employed if desired. The amounts and classes of surfactant used in compositions of the present invention are selected to provide high levels of herbicidal efficacy and a stable single-phase homogenous mixture in the case of a liquid formulation. The invention is also applicable to solid formulations.

A composition of the invention can optionally comprise other additives such as ammonium sulfate, potassium sulfate, potassium chloride, sodium sulfate, urea, or mixtures thereof. A contemplated composition can optionally include a synergist, quick-burn additive, humectant, co-herbicide, dye, pigment, corrosion inhibitor, thickener, dispersing agent, calcium sequestrant, defoamer, antifreeze, pour-point depressant, or mixture thereof. Preferably, additives used in compositions of the present invention possess sufficient solubility or dispersibility in a concentrated aqueous glyphosate solution to allow desired concentrations to be attained.

Where a co-herbicide is included in the formulation, it is preferred that the co-herbicide be water-soluble. Examples of suitable co-herbicides are the salts of sulfonylurea, glufosinate, acifluorfen, asulam, benazolin, bentazon, bialaphos, bromacil, bromoxynil, chloramben, clopyralid, 2,4-D, 2,4-DB, dalapon, dicamba, dichlorprop, diclofop, diquat, endothall, fenac, fenoxaprop, flamprop, fluazifop, fluoroglycofen, fomesafen, fosamine, haloxyfop, imazameth, imazamethabenz, imazamox, imazapyr, imazaquin, imazethapyr, ioxynil, MCPA, MCPB, mecoprop, methylarsonic acid, naptalam, nonanoic acid, paraquat, picloram, sulfamic acid, 2,3,6-TBA, TCA and triclopyr. A preferred co-herbicide is the IPA salt of 2,4-D. Alternatively, at least one herbicidally active compound employed can be selected from the group above, with or without the inclusion of glyphosate.

One or more process aids known to the skilled artisan can also be employed in the formulations of the present invention. Glycols are a preferred process aid. The preferred glycols include, but are not limited to propylene glycol, diethylene glycol, ethylene glycol, dipropylene glycol, mixtures thereof and the like. An example of a composition of the invention contains ammonium glyphosate in an amount of about 450 to about 500 g a.e./l, together with about 3% to about 5.2% by weight of methyl bis(2-hydroxyethyl)cocoammonium chloride, and about 0.75% to about 1.6% by weight of diethylene glycol. No nonionic surfactant is employed.

Formulations of the present invention may be generally prepared by mixing the glyphosate technical, together with other ingredients in a suitable mixing vessel with agitation, such as a blender. Heating maybe needed to facilitate mixing.

This invention also relates to a herbicidal method of using a contemplated composition in an amount effective to kill or control unwanted vegetation by diluting the composition in water and applying the diluted composition to foliage of the vegetation to be killed or controlled.

Glyphosate formulations, as formulated in a composition of the invention, should be applied to plant foliage at an application rate sufficient to give the desired effect. Application rates are usually expressed as amount of glyphosate a.e. per unit area of land treated, e.g. grams a.e. per hectare (g a.e./ha). What constitutes a "desired effect" varies according to the standards and practice of those who investigate, develop, market and use glyphosate products. For example, the amount of glyphosate a.e. applied per unit area to give, consistently and reliably, at least 85% control of a plant species as measured by growth reduction or mortality is often used to define a commercially effective rate.

Preferred compositions of the invention provide enhanced herbicidal effectiveness by comparison with commercial standard formulations of glyphosate "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific glyphosate formulation, such as a formulation of the present invention, is within the skill of the ordinary agricultural scientist. Those of skill in the art will likewise recognize that individual plant conditions, weather and growing conditions, as well as the specific formulation selected, will influence the degree of biological effectiveness achieved in practicing this invention. Useful application rates can therefore depend upon all of the above conditions. Much information is known about appropriate application rates for glyphosate formulations in general. Over two decades of glyphosate use and published studies relating to such use have provided abundant information from which a weed control practitioner can select glyphosate application rates that are herbicidally effective on particular species at particular growth stages in particular environmental conditions.

Various application methods may be employed including broadcast spraying, directed spraying or wiping the foliage with a diluted composition of this invention. Depending on the degree of control desired, the age and species of the plants, weather conditions and other factors, typically the glyphosate application rate is a herbicidally effective amount of about 0.1 to about 10 kg a.e./ha and preferably from about 0.25 to about 2.5 kg a.e./ha, although greater or lesser amounts may be applied.

Herbicidal compositions of glyphosate or derivatives thereof are used to control a very wide variety of plants worldwide. Glyphosate compositions of the invention can be applied to a plant in a herbicidally effective amount, and can effectively control one or more plant species of one or more of the following genera without restriction: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*.

Particularly important annual broadleaf species for which glyphosate compositions are used are exemplified without limitation by the following: velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.)

Particularly important annual narrowleaf species for which glyphosate compositions are used are exemplified without limitation by the following: wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial broadleaf species for which glyphosate compositions are used are exemplified without limitation by the following: mugwort (*Artemisia* spp.), milkweed (*Asclepias* spp.), canada thistle (*Cirsium arvense*), field bindweed (*Convolvulus arvensis*) and kudzu (*Pueraria* spp.).

Particularly important perennial narrowleaf species for which glyphosate compositions are used are exemplified without limitation by the following: brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial species for which glyphosate compositions are used are exemplified without limitation by the following: horsetail (*Equisetum* spp.), bracken (*Pteridium aquilinum*), blackberry (*Rubus* spp.) and gorse (*Ulex europaeus*).

Thus, glyphosate compositions of the present invention, and a method for treating plants with such compositions, can be useful on any of the above species. In a particular contemplated method of use, a composition of the invention comprising glyphosate and surfactant is applied to foliage of crop plants genetically transformed to tolerate glyphosate, and simultaneously to foliage of weeds or undesired plants growing in close proximity to such crop plants. This process results in control of the weeds or undesired plants while leaving the crop plants substantially unharmed.

Application of diluted compositions to foliage of plants is preferably accomplished by spraying, using any conventional means for spraying liquids, such as spray nozzles, atomizers, or the like. Compositions of the present invention can be used in precision farming techniques, in which apparatus is employed to vary the amount of glyphosate applied to different parts of a field, depending on variables such as the particular plant species present, soil composition, and the like. In one embodiment of such techniques, a global positioning system operated with the spraying apparatus can be used to apply the desired amount of a diluted composition to different parts of a field.

A composition of the invention is preferably diluted to a sufficient degree in water to be readily sprayed using standard agricultural spray equipment. The rate per unit land area of diluted composition applied by spraying is conventionally known as "spray volume". Suitable spray volumes for the present invention vary depending upon a number of factors, including the plant species involved. Useful spray volumes for applying a diluted composition of the invention to foliage can range from about 25 to about 1,000 liters per hectare (l/ha), preferably about 50 to about 300 l/ha.

Particularly preferred formulations of the invention comprise stable aqueous liquid concentrates comprising an ammonium or diammonium salt of glyphosate and an alkoxylated quaternary alkylammonium salt surfactant. Formulations containing diammonium salts of glyphosate are particularly preferred. Generally, the molar ratio of ammonium ion to glyphosate ion in the formulation can range from about 0.8 to about 2.5. A ratio of ammonium ion to glyphosate ion of at least about 1.2 is preferred. Ammonium ion to glyphosate ion ratios between about 1.5 and about 2.2 may be particularly advantageous for some applications. Preferably, the formulation contains at least about 120 g/L, more preferably at least about 240 g/L, 300 g/L or 325 g/L, and still more preferably at least about 360 g/L glyphosate, a.e. In certain embodiments, the glyphosate a.e., content may be greater than about 400 g/L, greater than about 425 g/L or greater than about 450 g/L. The surfactant may correspond to the formula set forth above, or more generally to the formula:

$$RR'N^{(+)}AB$$

where R is a straight chain or branched chain, saturated or unsaturated alkyl group having from 8 to 22 carbon atoms, R' is a straight or branched chain, saturated or unsaturated alkyl group having from 1 to 4 carbon atoms, A is $(R^2O)_p(R^3O)_q(R^4O)_zR^8$ and B is $(R^5O)_{p'}(R^6O)_{q'}(R^7O)_{z'}R^9$ where each of $R^2$, $R^3$, $R^4$, $R^5$, $R^6$, and $R^7$ is independently selected from the group consisting of ethylene and isopropylene, each of $R^8$ and $R^9$ is independently selected from hydrogen, methyl and ethyl, and each of p, q, p', q', z and z' is independently an integer between 0 and 30 and p+p'+q+q'+z+z' is at least about 2.

The weight ratio of the sum of all said alkoxylated quaternary alkylammonium salt surfactant(s) to the sum of any polyalkylene oxide alkyl ether surfactant(s) is typically greater than 4.5:1, preferably greater than about 5.2:1, still more preferably greater than about 10:1 or 20:1. In certain especially preferred embodiments, the ammonium glyphosate concentrate is substantially devoid of any polyalkylene oxide alkyl ether surfactant, i.e., the concentration of the latter type of surfactant is below the level at which it has any functional effect as a surfactant and/or below the level at which it has any measurable effect on the cloud point of the formulation. It is also preferred that the weight ratio of the sum of all said alkoxylated alkyl quaternary alkylammonium salt surfactant(s) to the sum of all nonionic surfactants be greater than about 4.5:1, more preferably greater than about 5.2:1, and still more preferably greater than about 10:1 or 20:1. Advantageously, the ammonium glyphosate concentrate may be substantially devoid of any nonionic surfactant, "substantially devoid" being understood as described above.

For many applications, it is preferred that the sum of (p+p'+q+q'+z+z')=2, i.e., that the surfactant is a 2EO dialkylammonium or other bis(hydroxyalkyl)dialkylammonium salt such as the bis(hydroxyethyl)methyl-cocoamine or bis (hydroxyethyl) methyltallowamine. For other applications, it may be preferred that (p+p'+q+q'+z+z')≥3. Where the quaternary alkylammonium salt is prepared by alkoxylation beyond the bis(hydroxyalkyl) species, the surfactant obtained is typically a mixture of homologs of varying extent of alkoxylation. Such surfactants can best be characterized by the number average value of (p+p'+q+q'+z+z'), sometimes referred to herein as $W_0$. For example, alkoxylated quaternary alkylammonium surfactants for some applications may have a number average $W_0$ value between about 3 and about 7, or more particularly between about 4 and about 6. In other instances, an alkoxylated quaternary alkylammonium salt may have a $W_0$ value between about 6 and about 15, or more particularly between about 8 and about 12. Some formulations may comprise combinations of alkoxylated quaternary alkylammonium surfactants, e.g., a surfactant having a relatively low value of $W_0$, for example about 2, or in the range of 3 to 7, and another surfactant having a relatively high value of $W_0$, for example, in the range of about 8 to about 15 or between about 8 and about 12.

In certain preferred embodiments of the invention, the dialkoxylated quaternary alkylammonium salt surfactant comprises a mixture of homologs wherein R contains an average of between about 16 and about 18 carbon atoms. In certain particularly preferred embodiments, R is derived from tallow.

It has been found that stable aqueous liquid concentrates comprising diammonium glyphosate and dialkoxylated quaternary alkylammonium salt surfactants may be formulated at concentrations in excess of 38.0 wt. % glyphosate, a.e., and that such concentrates may exhibit a pH less than 7.3 and an ammonia concentration over the solution of less than about 750 ppm at 25° C.

In the ammonium glyphosate formulations of the invention, the weight ratios of glyphosate, a.e., to alkoxylated quaternary alkylammonium salt are typically between about 3 and about 20, more typically between about 3 and about 10. Particularly suitable diammonium glyphosate formulations may be prepared having a glyphosate to alkoxylated quaternary alkylammonium salt surfactant ratio between about 3.5 to about 9. Expressed on the basis of the total concentrate, the concentration of the sum of alkoxylated quaternary alkylammonium salt surfactant(s) may typically range from about 3 wt. % to about 12 wt. %, more typically from about 3.5 wt. % to about 10 wt. %.

The preferred ammonium glyphosate concentrates of the invention may also be formulated without substantial proportions of either ammonium sulfate or an alkylene glycol such as ethylene glycol or propylene glycol, or an alkylene ether glycol such as diethylene glycol.

For example, the ammonium sulfate content may be less than about 5 wt. %, less than about 3 wt. %, less than about 2 wt. % or less than about 1 wt. %. In fact, the concentrate may be substantially devoid of ammonium sulfate.

Similarly, the weight ratio of the sum of dialkoxylated quaternary alkylammonium salt surfactant to alkylene glycol and/or alkylene ether glycol may be greater than about 3.25, and is preferably greater than about 4, typically greater than about 5, and more typically greater than about 6, 8 or 10. The ratio of the sum of dialkoxylated quaternary alkylammonium salt surfactant to the sum of (all polyalkylene oxide alkyl ether surfactants+alkylene glycols+alkylene ether glycols) is greater than about 2, preferably greater than about 3, typically greater than about 5, 8 or 10.

Polyalkylene oxide alkyl ether surfactants have been used as to limit eye toxicity of glyphosate salt concentrates comprising alkoxylated quaternary alkylammonium salt surfactants, while alkylene glycols and alkylene ether glycols are typically present in glyphosate concentrates that comprise alkoxylated quaternary alkylammonium salt and polyoxyethylene oxide alkyl ether surfactants. It has been discovered that the ammonium glyphosate concentrates of the present invention may be formulated with minimal concentrations of nonionic surfactants, minimal concentrations of alkylene ether glycols, minimal concentrations of alkylene ether glycols, or with minimal concentrations of either nonionic surfactants, alkylene glycols, or alkylene ether glycols. Certain preferred formulations may be substantially devoid of each, any, and/or all of these.

The absence or substantial absence of polyalkylene oxide alkyl ethers and other nonionics contributes to the stability of the formulations, because nonionic surfactants can compromise the stability of ammonium glyphosate concentrates comprising alkoxylated alkylammonium salt surfactants. In accordance with the invention, it has been discovered that diammonium glyphosate concentrates containing, e.g., 2EO, 5 EO and 10 EO methylcocoquats and methyltallowquats can be formulated without either a nonionic surfactant, an alkylene glycol, or an alkylene ether glycol.

Further in accordance with the invention, it has been discovered that aqueous liquid ammonium glyphosate concentrates having surprisingly low eye toxicity can be formulated with minimal concentrations of polyalkylene oxide alkyl ethers or other nonionic surfactants. In fact, it has been found that such low eye toxicity formulations can be substantially devoid of nonionic surfactants. Prior to the present invention, it had been understood that, to meet the eye toxicity standards of at least some jurisdictions without incorporating a significant fraction of nonionic surfactant, the concentrations of cationic surfactants in ammonium glyphosate concentrates must be maintained at levels significantly lower than those desired for herbicidal efficacy. For example, it had been understood that, in an ammonium glyphosate concentrate having a loading greater than about 360 g/L glyphosate, a.e., the total concentration of dialkoxylated quaternary alkylammonium salt surfactant(s) should be maintained at not greater than about 3.5 wt. %, preferably not greater than about 3.2 wt. %, and/or that the weight ratio of such surfactant(s) to glyphosate, a.e., should be not greater than about 0.28, preferably not greater than about 0.25, typically not greater than about 0.20, 0.15, 0.13, 0.10 or 0.08. However, in accordance with the invention, it has been found that low eye toxicity can be preserved at significantly higher surfactant concentration where certain novel principles are observed with regard to the formulation of the concentrate.

More particularly, it has been found that eye toxicity can be controlled by controlling the molar concentration of alkoxylated quaternary alkylammonium ion in the aqueous liquid concentrate, even at weight concentrations of alkoxylated quaternary alkylammonium salt sufficient to substantially enhance herbicidal efficacy. This may be achieved by selection of an alkoxylated quaternary alkylammonium salt surfactant having an average molecular alkylene oxide to amine ratio ($W_0$) in an intermediate range, thereby effectively diluting the molar concentration of quaternary ammonium ion as compared to a surfactant having a low value of $W_0$ in the range of, say, 2 to 4. Selection of a quaternary ammonium salt surfactant of such intermediate $W_0$ value thus achieves a relatively modest molar concentration of alkoxylated quaternary alkylammonium ion by what may be referred to as "intramolecular dilution." In various alternative embodiments, a high degree of herbicidal efficacy may be maintained at low levels of eye toxicity by "intermolecular dilution," i.e., by blending a relatively low molecular weight alkoxylated quaternary alkylammonium salt having a $W_0$ value in the range between about 2 and about 4 with a relatively high molecular weight alkoxylated quaternary alkylammonium salt having a $W_0$ value between about 7 and about 15.

Preferably, the R substituent in the formula set forth above comprises between about 8 and about 18 carbon atoms, more preferably between about 12 to about 18 carbon Thus, an alkoxylated quaternary alkylammonium ion of intermediate $W_0$ value of about 5 to about 8 typically has a molecular weight between about 375 and about 650 preferably between about 400 and about 650 Expressed in another manner, a 5 to 8 EO ethoxylated quaternary alkylammonium chloride surfactant corresponding to the formula set forth above and derived from coconut or tallow has a "diluted" N content between about 0.0015 moles and about 0.0025 moles per gram surfactant. Such selection of relatively high molecular weight surfactants of intermediate $W_0$ values allows relatively high weight concentrations of alkoxylated quaternary alkylammonium surfactant to be incorporated into an aqueous ammonium glyphosate concentrate without exceeding the molar concentrations of the surfactant as described hereinabove. Without being held to a particular theory, it is also believed that the relatively high molecular weight alkyl and alkylene oxide substituents serve to reduce activity of the positively charged quaternary ammonium ion at a given concentration thereof, which may permit a slightly higher surfactant loading to be used for better bioefficacy, without causing excessive eye irritation.

Based on the same preferred ranges of R substituents, a $C_{12}$ to $C_{18}$ alkoxylated quaternary alkylammonium salt having a low $W_0$ value between about 2 and about 4 typically has a molecular weight in the range between about 270 and about 450, and a $C_{12}$ to $C_{18}$ alkoxylated quaternary alkylammonium salt having a relatively high $W_0$ value between about 7 and about 15 has a molecular weight in the range between about 490 and about 925. Thus, for example, a blend having a weight ratio of a 2-4 EO methylcocoamine to 7-15 EO methylcocoamine or methyltallow amine between about 1:2 and 2:1 preferably comprises a diluted N content between about 0.0010 and about 0.0030, more preferably between about 0.0015 and about 0.0025, moles per gram surfactant.

Specific examples of blended alkoxylated quaternary alkylammonium salts include blends of an ethoxylated N-methylcocoammonium chloride sold under the trade designation "Ethaquad C12" having a $W_0$ value of 2 and a molecular weight of about 323 (quaternary 2 EO N-methylcocoammonium ion MW=287; chloride ion MW=35.5) and an ethoxylated N-methylcocoammonium chloride having a $W_0$ value of 10 and a molecular weight of 539 (quaternary 10 EO N-methylcocoammonium ion MW=503; chloride ion MW=35.5) or ethoxylated N-methyltallowammonium chloride having a $W_0$ value of 10 and a molecular weight of 759 (quaternary 10 EO N-methyltallowammonium ion MW=723; chloride ion MW=35.5).

Exemplary diammonium formulations that are substantially devoid of any nonionic surfactant are set out below:

Formulation A (360 g/L a.e.)

| | |
|---|---|
| Diammonium glyphosate | 30.3 wt. %, a.e. |
| N-methylcocoquat 2EO | 7.90% a.i. |

Formulation B (360 g/L a.e.)

-continued

| | |
|---|---|
| Diammonium glyphosate | 30.3 wt. %, a.e. |
| N-methyltallowquat 10 EO | 2.60 wt. %, a.i. |
| Methylcocoquat 2EO | 2.50 wt. % a.i. |
| Formulation C (360 g/L) | |

| | |
|---|---|
| Diammonium glyphosate | 30.3 wt. %, a.e. |
| N-methylcocoquat 5EO | 5.1 wt. %, a.i. |
| Formulation D (480 g/L) | |

| | |
|---|---|
| Diammonium glyphosate | 38.4 wt. %, a.e. |
| N-methylcocoquat 2EO | 7.2 wt. %, a.i. |
| Formulation E (480 g/L) | |

| | |
|---|---|
| Diammonium glyphosate | 38.4 wt. %, a.e. |
| N-methylcocoquat 2EO | 4.62 wt. %, a.i. |
| Formulation F (360 g/L a.e.) | |

| | |
|---|---|
| Diammonium glyphosate | 30.3 wt %, a.e. |
| N-methylcocoquat 2EO | 2.00 wt %, a.i. |
| N-methylcocoquat 10EO | 3.10 wt %, a.i. |
| Moles Quat N | 0.123 |
| Formulation G (360 g/L a.e.) | |

| | |
|---|---|
| Diammonium glyphosate | 30.3 wt %, a.e. |
| N-methylcocoquat 2EO | 2.60 wt %, a.i. |
| N-methyltallowquat | 2.50 wt %, a.i. |
| Moles Quat N | 0.119 |
| Formulation H (360 g/L a.e.) | |

| | |
|---|---|
| Diammonium glyphosate | 30.3 wt %, a.e. |
| N-methyltallowquat 5EO | 5.10 wt %, a.i. |
| Tergitol nonionic surfactant | 1.00 wt %, a.i. |
| C12, 14 Linear Alcohol (Tergitol) | 9 mol EO |
| Formulation I (480 g/L a.e.) | |

| | |
|---|---|
| Diammonium glyphosate | 38.4 wt %, a.e. |
| N-methylcocoquat 2EO | 4.65 wt %, a.i. |
| Nonionic surfactant | 1.00 wt %, a.i. |
| OSP C18 Alcohol | 9 mol EP 30 mol PO |

All of these are brought to 100% with deionized water. The ammonium ion to glyphosate ion ratio is 1.9:1.

Of the formulations set forth above, Formulations B, C, F, G and H are of exceptionally low eye toxicity. These achieved a favorable rating of "yellow" according to the Acute Eye Irritation test per guideline OPPTS 870.2400 as issued by the United States Environmental Protection Agency, EPA712-L-96-195, August 1998. These results contrast with the typical rating of "red" for high load ammonium glyphosate concentrates containing alkoxylated quaternary alkylammonium salts in the absence of relatively high concentrations of nonionic surfactants, or at least high nonionic to alkoxylated quaternary alkylammonium salt ratios.

The invention will now be illustrated by the following nonlimiting examples.

EXAMPLES

Three examples were performed by two different testing agents at three different times. Three replicas were used. The spray rate was in g a.e./H (grams of glyphosate acid per hectare). If the spray rate was the same, the glyphosate concentration was the same. All were sprayed with diluted solutions (from concentrates) and with the same spray volume. The percent control (% Control) was compared in all samples at 21 DAT (days after treatment).

Since it is the glyphosate anion that is biologically active, the concentration of a glyphosate formulation is typically expressed as grams of glyphosate acid per liter (g a.e./l) at 25 C. Because of this, people compare glyphosate formulations generally at the same g a.e./l. The concentration of surfactant is typically expressed as grams of active surfactant per liter (g/l). Sometimes acid:surfactant ratio is also used. For example, if a formulation is 540 g a.e./l and surfactant is 90 g/l, the acid:surfactant ratio is 6. Therefore, the larger the acid:surfactant ratio, the less surfactant that is in the formulation.

Example 1

Figure 1:
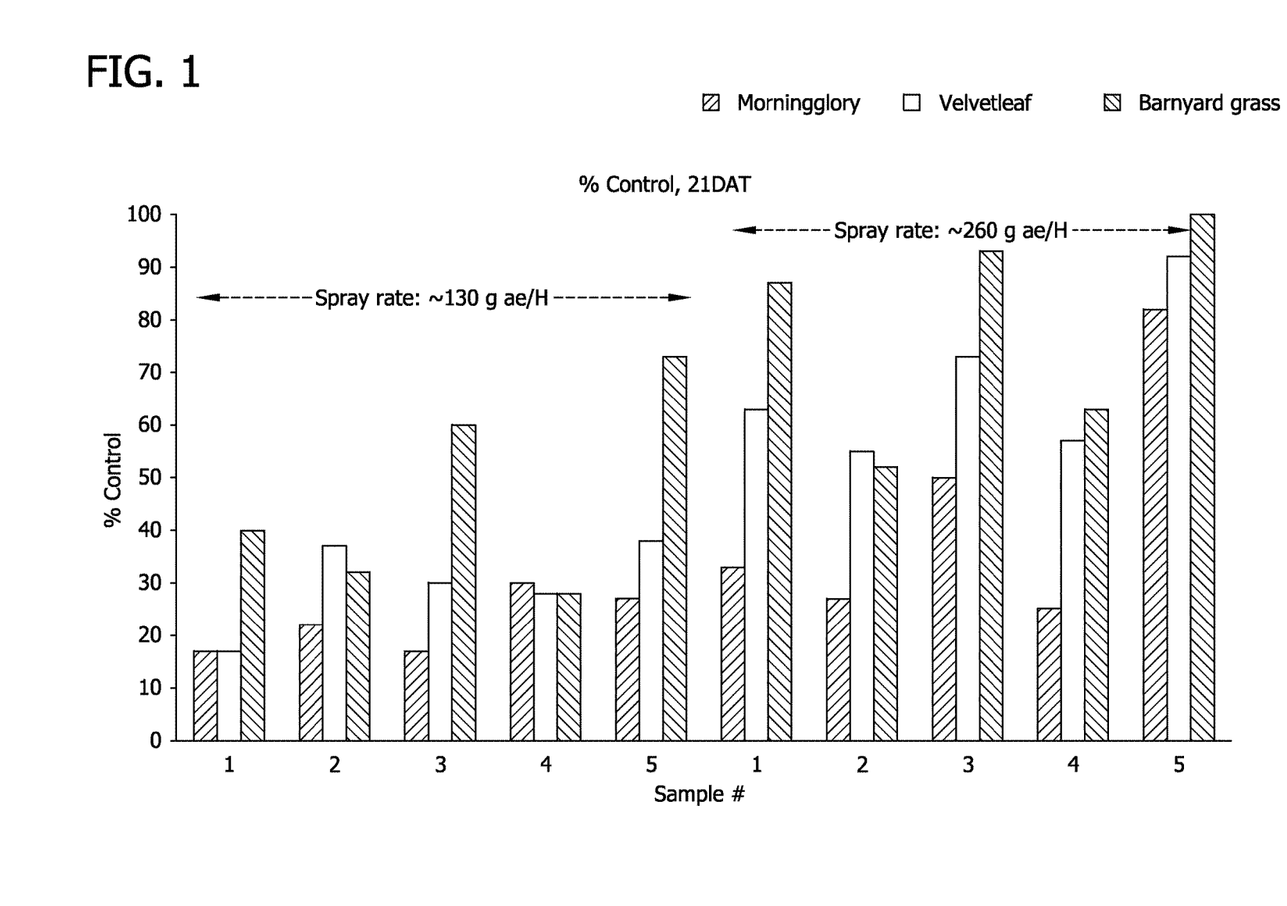
FIG. 1 displays results of testing described in Example 1.

Shown in FIG. 1 are five examples.

This example demonstrates that glyphosate without surfactant (Sample #2) did not provide the level of control as those with surfactants. In particular, Sample #5 had very low surfactant concentration, much lower than typical commercial products and lower than Sample #1, #3, and #4. However, Sample #5 still had higher % Control than all other samples. On the contrary, in order to achieve reasonable % Control, the surfactant system used in U.S. Pat. No. 5,998,332, cationic and nonionics blend (Samples #3 and #4), needed to be used at about an acid:surfactant ratio of 4.3:1, a concentration more than twice as concentrated as that in Sample #5. At the same glyphosate concentration, the level of control provided by Sample #3 was less than for Sample #5 even though it had a surfactant concentration at twice the level found in Sample #5.

Example 2

Figure 2:
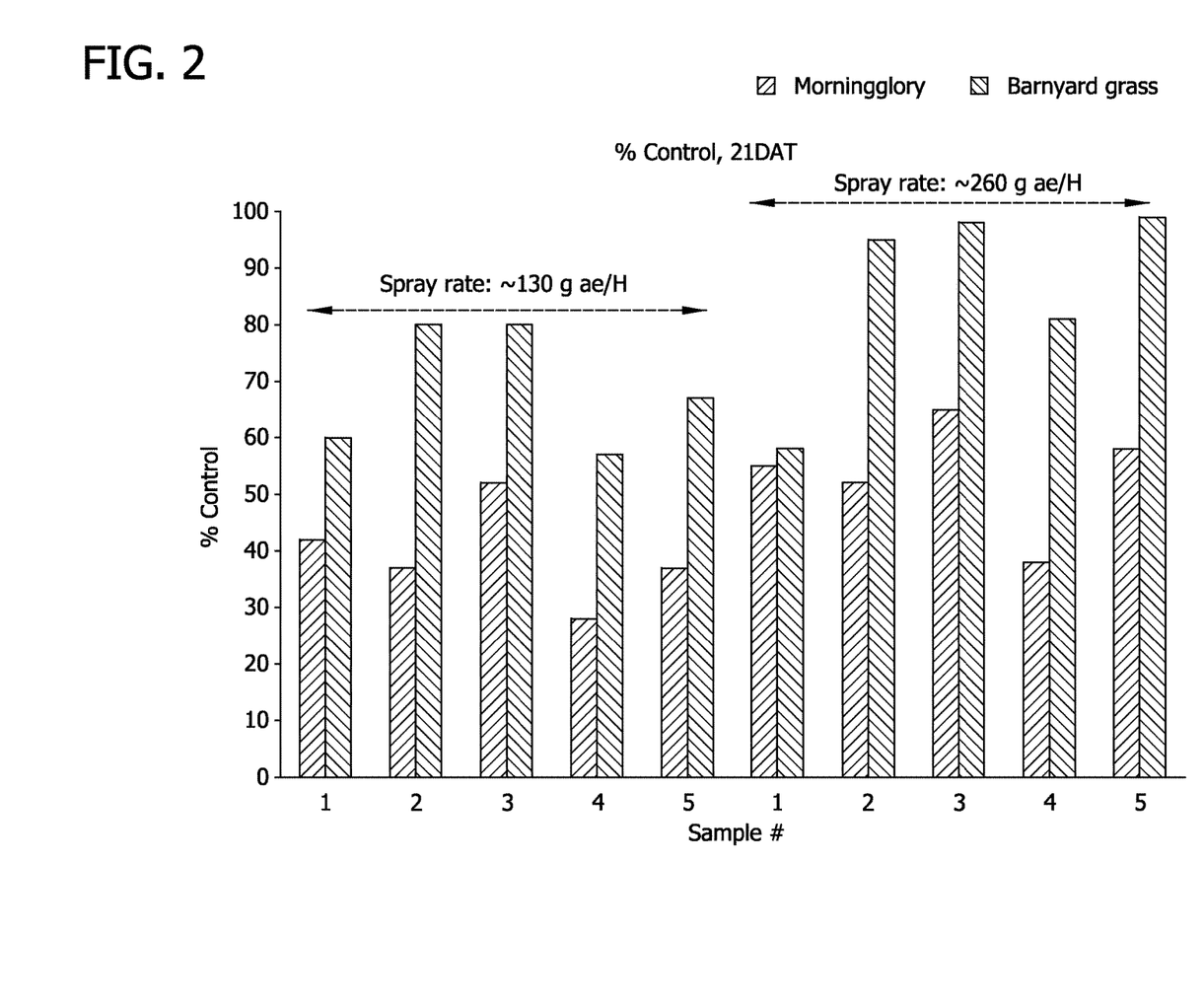
FIG. 2 displays results of testing described in Example 2.

Shown in FIG. 2 are five samples. All were potassium glyphosate salt:

In this example, Sample #3 had very low surfactant concentration, much lower than typical commercial products and lower than Samples #2, #4 and #5. However, Sample #3 still had higher or equivalent % Control than all other samples. At the same glyphosate concentration, Sample #3 had equivalent control to Sample #5 in % Control even though it had a surfactant concentration twice less concentrated than Sample #5.

Moreover, only Sample #3 was stable between −20 and 60 C at a concentration of more than 540 g a.e./l.

Example 3

Figure 3:
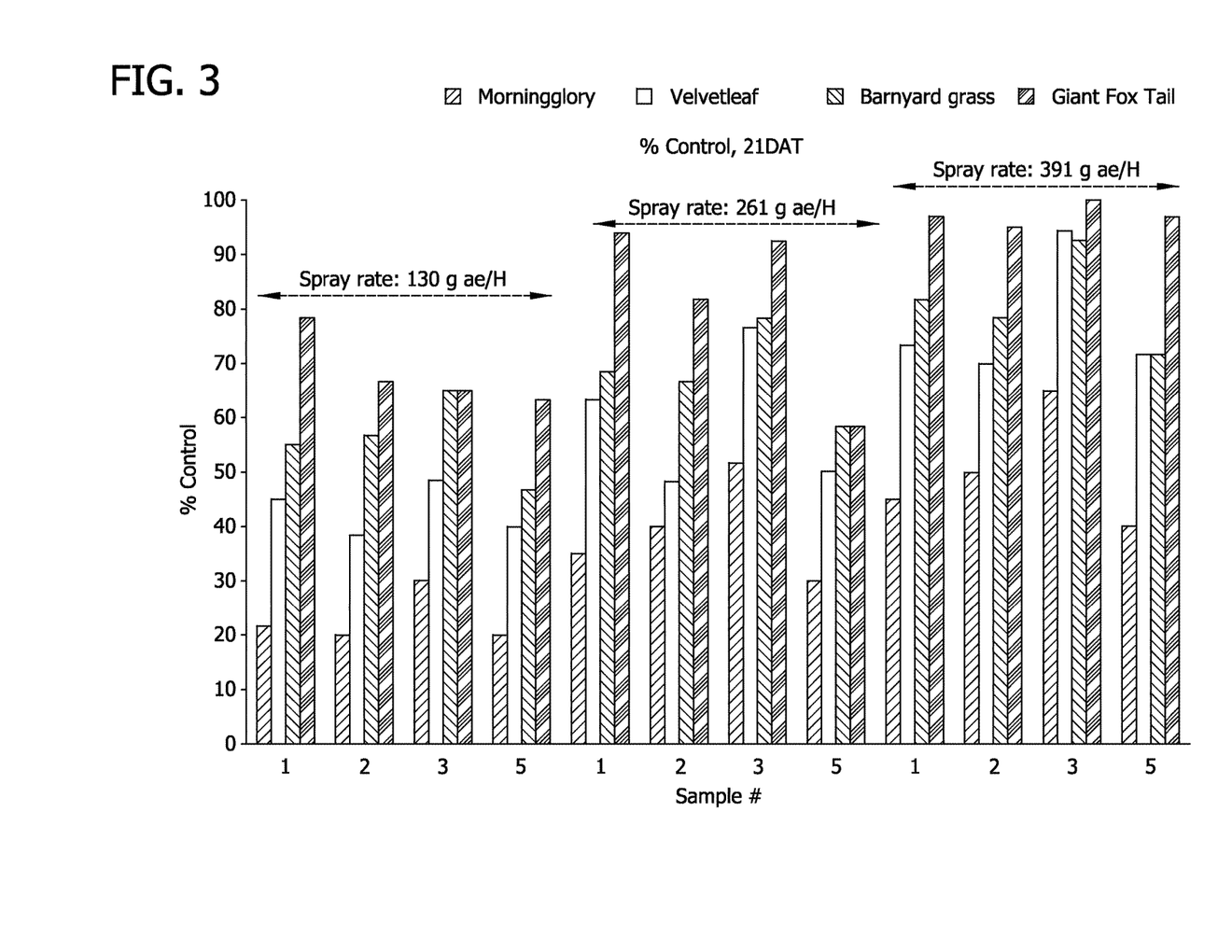
FIG. 3 displays results of testing described in Example 3.

Samples shown in FIG. 3 were the same as those in Example 2 (Sample #4 is not used here). Again, in this example, Sample #3 was equivalent to or better than the other samples in % Control.

As is shown in the above examples, it has been unexpectedly discovered that a highly effective and efficient surfactant, alkoxylated alkylamine quaternary, can improve significantly the efficacy of a glyphosate formulation. Moreover, the alkoxylated alkylamine quaternary surfactant is stable in all salts of glyphosate formulations (including potassium and ammonium) even at very high concentration (470-600 g a.e./l). This result is expected to provide significant cost savings in raw material for glyphosate formulations and will improve the logistics of handling surfactants in the plant.

What is claimed is:

1. A stable aqueous liquid herbicidal concentrate comprising an ammonium salt of glyphosate and containing at least about 120 g/L glyphosate a.e., ammonium ion in a molar ratio to glyphosate between about 0.75 and about 2.5, and at least two alkoxylated quaternary alkylammonium surfactants corresponding to the formula:

$RR'N^{(+)}AB$ where R is a straight chain or branched chain, saturated or unsaturated alkyl group having from 8 to 22 carbon atoms, R' is a straight or branched chain, saturated or unsaturated alkyl group having from 1 to 4 carbon atoms, A is $(R^2O)_p(R^3O)_q(R^4O)_zR^8$ and B is $(R^5O)_{p'}(R^6O)_{q'}(R^7O)_{z'}R^9$ where each of $R^2$, $R^3$, $R^4$, $R^5$, $R^6$, and $R^7$ is independently selected from the group consisting of ethylene and isopropylene, each of $R^8$ and $R^9$ is independently selected from the group consisting of hydrogen, methyl, and ethyl, and each of p, q, p', q', z and z' is independently an integer between 0 and 30 and the sum of (p+p'+q+q'+z+z') is at least about 2, the weight ratio of the total of said at least two alkoxylated quaternary alkylammonium surfactants to ammonium glyphosate, a.e., in said concentrate being between about 0.1:1 and about 0.2:1, and the average sum of (p+p'+q+q'+z+z') for one of said at least two surfactants being between about 2 and about 5, and the average sum of (p+p'+q+q'+z+z') for another of said at least two surfactants being between about 5 and about 15, wherein the concentrate further comprises a nonionic surfactant and wherein the weight ratio of the sum of said at least two alkoxylated quaternary alkylammonium surfactants to the nonionic surfactant is greater than 4.5:1.

2. The aqueous liquid herbicidal concentrate of claim 1 wherein the weight ratio of the sum of said one and said another surfactants to ammonium glyphosate, a.e., being between about 0.1:1 and about 0.2:1.

3. The aqueous liquid herbicidal concentrate of claim 2 wherein the weight ratio of said one surfactant to said another surfactant is between about 1:1.5 and about 1.5:1.

4. The aqueous liquid herbicidal concentrate of claim 1 wherein the mole ratio of alkoxylated quaternary alkylammonium surfactants to glyphosate is not greater than about 0.2:1.

5. The aqueous liquid herbicidal concentrate of claim 1 wherein the weight ratio of alkoxylated quaternary alkylammonium surfactants to glyphosate is between about 0.1:1 and about 0.17:1.

6. The aqueous liquid herbicidal concentrate of claim 1 wherein the molar concentration of alkoxylated quaternary alkylammonium ion in said aqueous concentrate is not greater than about 0.15.

7. The aqueous liquid herbicidal concentrate of claim 1 wherein the total molar concentration of all quaternary ammonium ions is not greater than about 0.15.

8. The aqueous liquid herbicidal concentrate of claim 1 comprising glyphosate in a concentration of at least 325 grams a.e. per liter.

9. The aqueous liquid herbicidal concentrate of claim 1 comprising glyphosate in a concentration of at least 360 grams a.e. per liter.

10. The aqueous liquid herbicidal concentrate of claim 1 comprising glyphosate in a concentration of at least 400 grams a.e. per liter.

11. The aqueous liquid herbicidal concentrate of claim 1 comprising greater than 38.0 wt. % of glyphosate a.e. and having a pH of less than 7.3.

12. The aqueous liquid herbicidal concentrate of claim 1 wherein the molar ratio of ammonium ions to glyphosate ions is at least about 1.2.

13. The aqueous liquid herbicidal concentrate of claim 1 wherein the molar ratio of ammonium ions to glyphosate ions is at least about 1.5.

14. The aqueous liquid herbicidal concentrate of claim 1 further comprising a co-herbicide.

15. The aqueous liquid herbicidal concentrate of claim 14 wherein said co-herbicide is selected from the group consisting of sulfonylurea, acifluorfen, asulam, benazolin, bentazon, bialaphos, bromacil, bromoxynil, chloramben, clopyralid, 2,4-D, 2,4-DB, dalapon, dicamba, dichlorprop, diclofop, diquat, endothall, fenac, fenoxaprop, flamprop, fluazifop, fluoroglycofen, fomesafen, fosamine, glufosinate, haloxyfop, imazameth, imazamethabenz, imazamox, imazapyr, imazaquin, imazethapyr, ioxynil, MCPA, MCPB, mecoprop, methylarsonic acid, naptalam, nonanoic acid, paraquat, picloram, sulfamic acid, 2,3,6-TBA, TCA, triclopyr, salts thereof, and mixtures thereof.

16. The aqueous liquid herbicidal concentrate of claim 1 wherein the average sum of (p+p'+q+q'+z+z') for at least one of said alkoxylated quaternary alkylammonium surfactants is between about 6 and about 15.

17. The aqueous liquid herbicidal concentrate of claim 16 wherein the average sum of (p+p'+q+q'+z+z') for at least one of said alkoxylated quaternary alkylammonium surfactants being about 2, and the average sum of (p+p'+q+q'+z+z') for another of said alkoxylated quaternary alkylammonium surfactants being in the range of between about 8 and about 15.

18. The aqueous liquid herbicidal concentrate of claim 1 wherein R of at least one of said alkoxylated quaternary alkylammonium surfactants contains an average between about 16 and about 18 carbon atoms.

19. The aqueous liquid herbicidal concentrate of claim 18 wherein R of each of said alkoxylated quaternary alkylammonium surfactants contains an average of between about 16 and about 18 carbon atoms.

20. The aqueous liquid herbicidal concentrate of claim 1 wherein R of at least one of said alkoxylated quaternary alkylammonium surfactants is derived predominantly from tallow.

21. The aqueous liquid herbicidal concentrate of claim 1 wherein one of said alkoxylated quaternary alkylammonium surfactants is methyl bis(2-hydroxyethyl)coco ammonium chloride.

22. The aqueous liquid herbicidal concentrate of claim 1 wherein the concentration of the sum of said alkoxylated quaternary alkylammonium surfactants is between about 3 wt. % and about 12 wt. % of the composition as a whole.

23. The aqueous liquid herbicidal concentrate of claim 1 wherein the concentration of the sum of said alkoxylated quaternary alkylammonium surfactants is between about 3.5 wt. % and about 10 wt. % of the composition as a whole.

24. The aqueous liquid herbicidal concentrate of claim 1 wherein the molar concentration of said alkoxylated quaternary alkylammonium surfactant is not greater than 0.25 moles/L.

25. The aqueous liquid herbicidal concentrate of claim 1 having a Red Band eye toxicity classification of yellow.

26. The aqueous liquid herbicidal concentrate of claim 1 having an ammonia concentration over the solution that is less than 750 ppm at 25° C.

27. The aqueous liquid herbicidal concentrate as set forth in claim 1 wherein the nonionic surfactant is a polyalkylene oxide alkyl ether surfactant.

28. The aqueous liquid herbicidal concentrate as set forth in claim 1 wherein the nonionic surfactant is a polyoxyethylene alkyl ether.

29. The aqueous liquid herbicidal concentrate as set forth in claim 1 wherein the weight ratio of the sum of said alkoxylated quaternary alkylammonium surfactants to the nonionic surfactant is greater than 5.2:1.

30. The aqueous liquid herbicidal concentrate as set forth in claim 29 wherein the nonionic surfactant is a polyoxyethylene secondary alcohol.

31. The aqueous liquid herbicidal concentrate as set forth in claim 1 wherein the weight ratio of the sum of said alkoxylated quaternary alkylammonium surfactants to the nonionic surfactant is greater than 10:1.

* * * * *